United States Patent
Chazan et al.

[11] 3,981,861
[45] Sept. 21, 1976

[54] ANTIBIOTIC AMINOGLYCOSIDES, PROCESSES OF PREPARATION AND PHARMACEUTICAL COMPOSITIONS

[75] Inventors: Jean Bernard Chazan, Paris; Daniel Coussediere, Villejuif; Jean-Claude Gasc, Bondy, all of France

[73] Assignee: Roussel-UCLAF, Paris, France

[22] Filed: Mar. 7, 1975

[21] Appl. No.: 556,405

[30] Foreign Application Priority Data
Mar. 12, 1975  France .................... 75.08314

[52] U.S. Cl. .................. 536/17; 424/180
[51] Int. Cl.² ........................ C07H 15/22
[58] Field of Search ............. 260/210 AB, 210 K

[56] References Cited
UNITED STATES PATENTS

| | | | |
|---|---|---|---|
| 3,753,973 | 8/1973 | Umezawa et al. | 260/210 AB |
| 3,878,193 | 4/1975 | Reimann | 260/210 AB |
| 3,925,354 | 12/1975 | Umezawa et al. | 260/210 AB |

OTHER PUBLICATIONS
Mallam et al., "The Jour. of Antibiotics," vol. XXVI, No. 12, pp. 782–783.

*Primary Examiner*—Johnnie R. Brown
*Attorney, Agent, or Firm*—Bacon & Thomas

[57] ABSTRACT

There are disclosed pharmaceutically-active aminoglycosides comprising 4-0-(2',6'-diamino 2', 3', 4', 6'-tetradesoxy α,D-erythrohexopyrannosyl) 6-0-(3''-methylamino 3'', 4'', 6''-tridesoxy α,D-xylohexopyrannosyl) 2-desoxystreptamine of the formula:

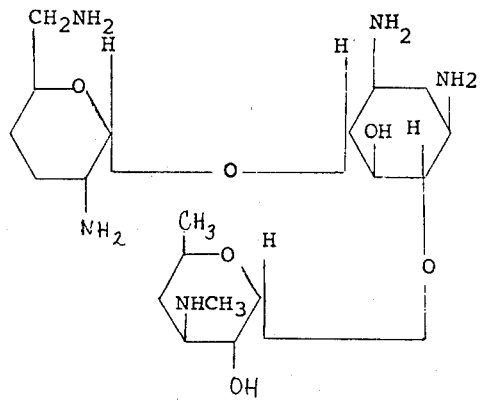

and the addition salts thereof with mineral acids or organic acids. Also disclosed are methods for preparation of the novel products as well as certain novel intermediate products. There are also disclosed pharmaceutical compositions in which the novel products are the active agents as well as methods for use of compositions as antibiotic agents.

5 Claims, No Drawings

ANTIBIOTIC AMINOGLYCOSIDES, PROCESSES OF PREPARATION AND PHARMACEUTICAL COMPOSITIONS

The present invention concerns new derivatives of aminoglycosides, their process of preparation. These compounds are pharmaceutically active as antibiotics. Thus, the main object of the present invention are new derivatives of aminoglycosides, namely 4-0-(2',6'-diamino 20',3',4',6'-tetradesoxy α,D-erythrohexopyrannosyl) 6-0-(3''-methylamino 3'',4'',6''-tridesoxy α,D-xylohexopyrannosyl) 2-desoxystreptamine of the formula:

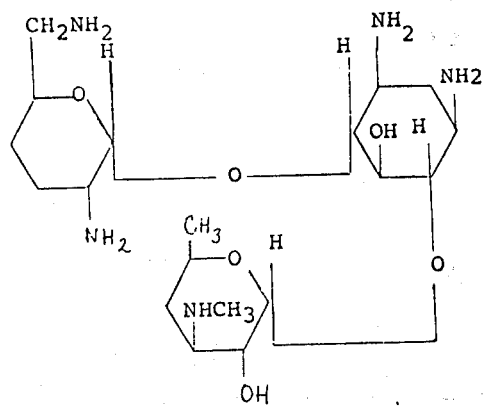

I as well as addition salts thereof with mineral or organic acids.

Such acid addition salts include, for example, chlorhydrate, bromhydrate, nitrate, sulfate, phosphate, acetate, formate, benzoate, maleate, fumarate, succinate, tartrate, citrate, oxalate, benzylate, glyoxylate, aspartate, alkylsulfonate such as methane sulfonate, arylsulfonate such as p-toluene sulfonate, or the like which are formed by using the corresponding acid. These salts include both those in which all of the amine nitrogens or only part of the amine nitrogens are satisfied.

Another object of the invention is the provision of pharmaceutical compositions particularly antibiotic compositions which include, as the active principle, the product of formula I or one of its therapeutically compatible salts.

The aforementioned products possess very interesting antibiotic activities on the bacteria gram (+) such as Staphylococci, Streptococci and notably penicillin resistant Staphylococci as well as on the bacteria gram (−), and notably coliform bacteria. Thus, they are useful in the treatment of humans and animals which are affected by these bacteria.

These properties render the product of formula I as well as its therapeutically compatible salts suitable for use as medication notably in the treatment of staphylococci such as those which are responsible for blood poisoning, skin diseases and infections on the face, pyodermites, septic and running sores, anthrax or carbuncles, phlegmons, erysipelas and the like. Also, acute staphylococci which arise in both the early stages and after influenza, bronchopneumonia, and other infections of the lung including lund congestion can be treated by the products of this invention. Further, the products of the invention can be used against collibacilloses.

These products can be used parenterally, orally, rectally or locally by topical application on the skin or mucous membrane.

They can be given in the form of injectable solutions or suspensions, sterile powders for improvised injectable preparations, tablets, capsules, syrups, suppositories, creams, pomades, and aerosol preparations. These pharmaceutical forms are prepared according to the standard processes. The usual dose, varying according to the product used, the subject treated, and the affection concerned, can be from 100 mg. to 1 gram per day in a normal human being when administered parenterally.

The invention also comprises a process preparation of the product of formula I above and of its salts, the process including a novel sequence of steps.

This process is characterized in that the product of formula

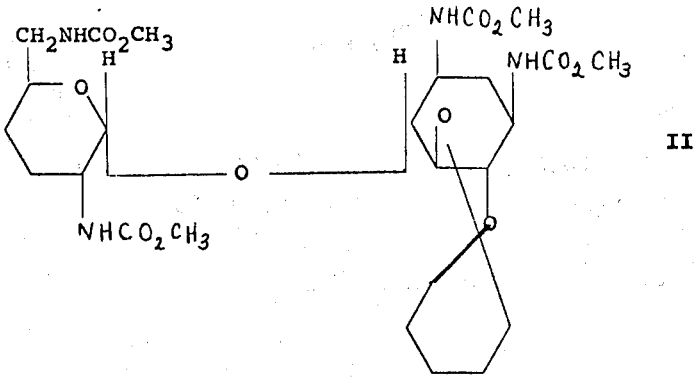

II is made to react with an acidic agent to obtain the product of the formula:

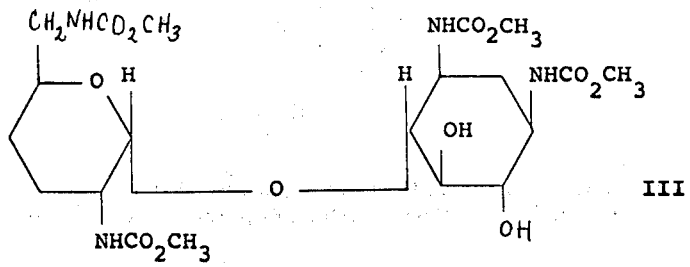

III which is reacted with a reagent of the formula:

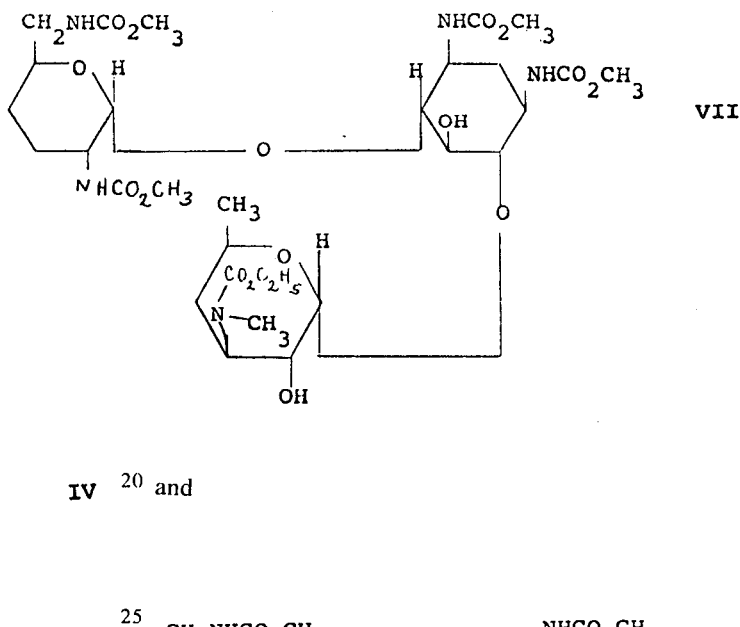

IV in the presence of a catalyst to obtain the corresponding product in the form of a mixture of α and β anomers of the formula:

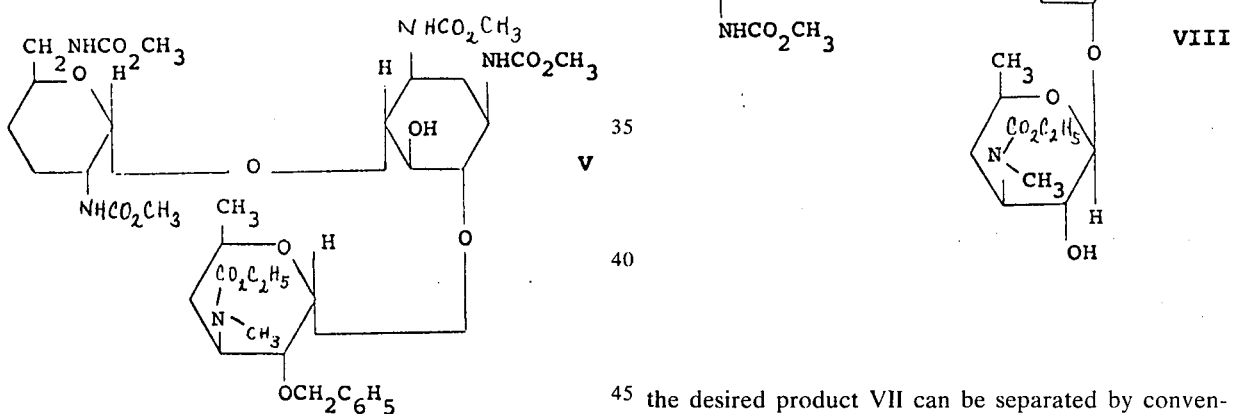

V and:

VI

This mixture is reduced with hydrogen in the presence of a catalyst to obtain a mixture of products having the formula:

VII and

VIII the desired product VII can be separated by conventional techniques and this mixture or the product VII is treated with an alkaline agent to obtain a mixture of products having the formula:

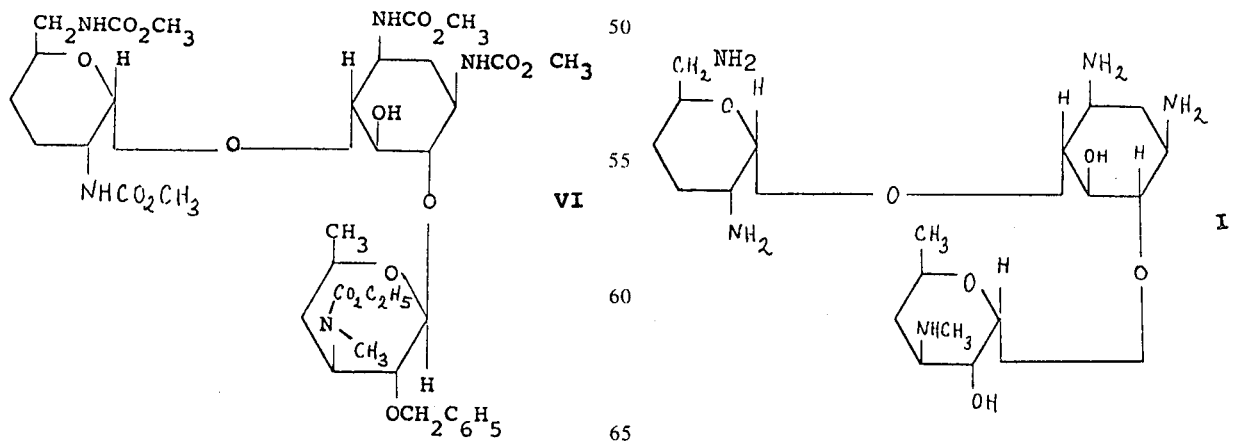

I

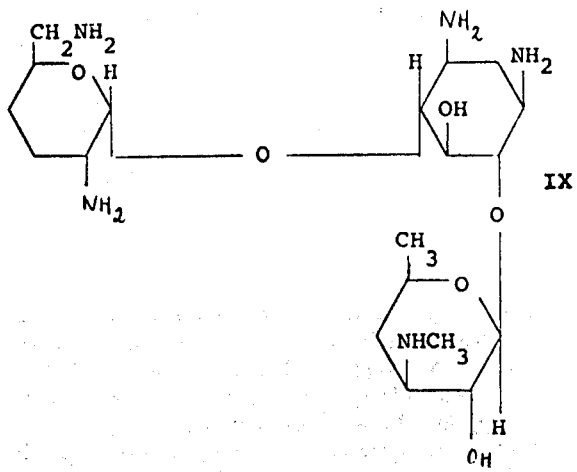

IX

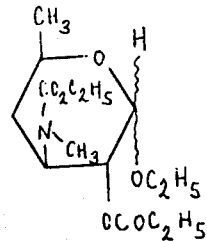

X which mixture is separated to give the product of formula I, or to obtain the product of formula I itself.

Then the product of formula I can be converted into an acid addition salt of an organic or inorganic acid.

The preferred operating conditions in the broad process described above are as follows: The preferred acidic agent which reacts with the product of formula II is advantageously an acidic ion exchange resin, or an aqueous solution of a mineral or organic acid which include for example, sulfuric acid, hydrochloric acid, acetic acid, formic acid or the like.

The reaction (condensation) between products III and IV is a named reaction referred to as KOENIGS - KNORR reaction and it is carried out in the presence of a catalyst which is preferably mercuric cyanide. Although, one can also use other mercury salts, a silver or cadmium salt, or a tertiary amine, such as collidine.

As the hydrogenation catalyst to transform the mixture of products of formula V and VI to a mixture of products of formulae VII and VIII it is advantageous to use palladium deposited on coal black, but one can also use other palladium or platinum salts, derivatives of platinum and other catalysts such as rhodium, ruthenium or nickel.

The alkaline agent which may be used to liberate the amine functions of the mixture of products of formulae VII and VIII is advantageously an aqueous solution of baryta (barium hydroxide) but other aqueous bases such as aqueous sodium or potassium hydroxide solutions may also be used.

The separation of the products of formulas VII and VIII or I and IX can be obtained by conventional procedures. The separation may preferably be obtained chromatographically using silica but alumina, cellulose, or magnesium silicate can be used. The separation can also be obtained by using fractional crystallization or countercurrent separation techniques. Different pure or aqueous organic solvents or mixtures of solvents may be used to satisfactorily make the separation.

The acid salt of compounds of formula I may be formed by conventional techniques. Acids which may be used for this include for example, hydrochloric, hydrobromic, nitric, sulfuric, phosphoric, acetic, formic, benzoic, maleic, fumaric, succinic, tartaric, citric, oxalic, benzylic glyoxylic, aspartic, alkane sulfonic, and arylsulfonic acids. The salification is preferably obtained in a solvent or a mixture of solvents such as water, ethers, such as ethyl ether, alcohols such as ethanol or ketones such as acetone.

The product of formula IV used in the process of the invention may be prepared according to the procedure as described in Belgian Pat. No. 814,724. This process is characterized by reacting a compound having a formula:

With an alkaline reagent at room temperature to obtain a product having the formula:

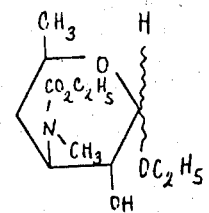

XI

This product is then treated with a benzyl halide in the presence of an alkaline agent to obtain a compound of the formula:

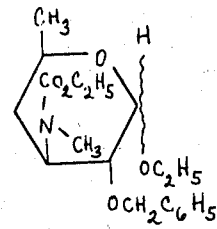

XII which is treated with acetic anhydride in acetic acid in the presence of a strong acid to obtain a producct of the formula

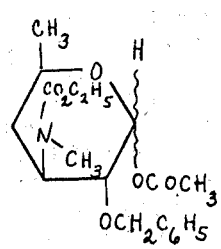

XIII

This product is then treated with anhydrous hydrochloric acid in the presence of acetyl chloride (an acyl halide) in an organic solvent medium to obtain the product of formula IV.

The wavy line which connects the substitutents on the carbon atom of the 1-position in formulae IV, X, XI, XII, and XIII indicates that these substitutents may be either $\alpha$ or $\beta$ to the ring. These products exist in the anomers $\alpha$ or $\beta$ or as a mixture of these.

Another object of the invention is the intermediate compound having the following formula:

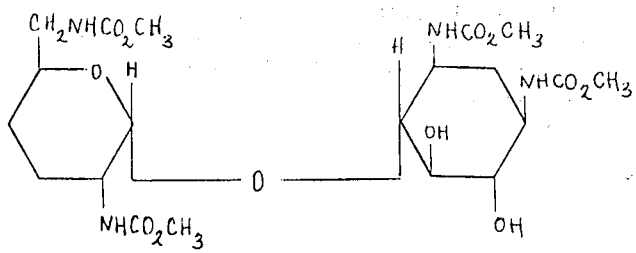

III which is particulary useful as an intermediate in the preparation of compounds of formula I.

The following examples illustrate the invention without in any way being limited thereon.

EXAMPLE 1

4-0-(2',6'-diamino 2',3',4',6'-tetradesoxy α,D-erythrohexopyrannosyl) 6-0-(3''-methylamino 3-,4'',6''-tridesoxy α,D-xylohexopyrannosyl) 2-desoxystreptamine Stage A: 3',4'-didesoxy N-tetracarbomethoxy neamine 54.6 grams of 3',4'-didesoxy 5,6-0-cyclohexylidene N-tetracarbomethoxy neamine (prepared according to J. of Antibiotics, 1971, 24, 711) are dissolved in 546 cm³ (ml) of methanol containing a sulfonic acid type ion exchange resin. The mixture was vigorously stirred for six hours and then filtered. The filtrate is dried under vacuum and the residue ground with isopropyl ether.

The residue is suspended in methylene chloride and isopropyl ether added with mixing to precipitate crystals of the product. The precipitate obtained is dried to give 37 grams of 3',4'-didesoxy N-tetracarbomethoxy neamine in the form of colorless crystals melting at 233°C [α]$_D^{20}$=+53° (c = 0.5%, dimethylformamide).

Stage B: 4-0-/2',6'-(N-carbomethoxy) diamino 2',-3',4', 6'-tetradesoxy α,D-erythrohexopyrannosyl/6-0-/2''-0-benzyl 3''-(N-carbethoxy N-methyl) amino 3'',-4'',6''-tridesoxy α,D-xylohexopyrannosyl/1,3-dimethyloxycarbonyl 2-desoxy streptamine.

20.5 grams of 1-0-acetyl 2-0-benzyl 3-(N-carbethoxy N-methyl) amino 3,4,6-tridesoxy D-xylohexopyranose are dissolved in 300 cm³ of dioxane containing 6% gaseous hydrochloric acid and 75 cm³ acetyl chloride. The temperature is raised to 37°C for 1½ hours and then evaporated under vacuum. The obtained residue is dissolved in 50 ml of dioxane and then added to 250 ml of dioxane containing 14 grams of 3',4'-didesoxy N-tetracarbomethoxy neamine at 60°C also containing 17 grams of mercuric cyanide. The mixture is agitated for 24 hours and then the dioxane is evaporated off. 150 ml of water are added and the mixture is extracted with methylene chloride. After drying the organic phase over sodium sulfate and it is evaporated to dryness, the resulting residue is chromatographically eluted on silica with a mixture of chloroform and acetone (6:4). 12.7 grams of 4-0-/2',6'-(N-carbomethoxy) diamino 2',3',4',6'-tetradesoxy α,D-erythropyrannosyl/6-0-/2''-0-benzyl 3''-(N-carbethoxy N-methyl) amino 3'',4'',6''-tridesoxy α,D-xylohexopyrannosyl/1,3-dimethyloxycarbonyl 2-desoxy streptamine. Thin layer chromatography gave a Rf = 0.4 (silica, chloroform-acetone 5:5).

The product obtained is a mixture of the two α and β anomers at the 1''-position.

Stage C: 4-0-/2',6'-(N-carbomethoxy) diamino 2',-3',4',6'-tetradesoxy α,D-erythrohexopyrannosyl/6-0-/3''-(N-carbethoxy N-methyl) amino 3'',4'',6''-tridesoxy α,D-xylohexopyrannosyl/1,3-dimethyloxycarbonyl 2-desoxy streptamine.

10.4 grams of the product obtained in the preceding step is dissolved in 120 ml of ethanol. 6 grams of 10% palladium on carbon catalyst and 0.7 ml concentrated hydrochloric acid was added. The mixture is mixed under a hydrogen atmosphere for 1 hour. The catalyst is separated from the mixture by filtration and the filtrate neutralized with a base ion exchange resin. The resin is separated from the filtrate and the resulting solution evaporated to dryness under vacuum. 7,9 grams of a mixture of anomer α and β are obtained. The mixture can be separated by chromatography using silica and eluted with 1:1 mixture of chloroform-acetone.

Anomere α: Rf. = 0,2 (silica, chloroform-acetone 1:1)

Anomere β: Rf. = 0.23 (silica, chloroform-acetone 1:1)

Stage D: 4-0-/2',6'-diamino 2',3',4',6'-tetradesoxy α,D-erythrohexopyrannosyl/6-0-/3''-methylamino 3'',4'',6''-tridesoxy αD-xylohexopyrannosyl/2-desoxystreptamine 7.9 grams of the product obtained in the preceding stage is dissolved in 30 ml of ethanol and to this solution is added a solution of 80 grams of hydrated baryta (barium hydroxide) in 100 ml of water containing 20 ml of ethanol with heating to 80°C. The mixture is stirred for six hours at 80°C followed by cooling and filtration of the reaction mixture. The pH of the filtrate is brought to 3 by the addition of standard sulfuric acid, filtered again and then neutralized with a base ion exchange resin. The resin is separated from the filtrate and the filtrate evaporated to dryness.

An amorphous product is obtained which is purified by passage through a column of ion exchange resin of the carboxylic acid type in the ammonium form by means of 0.2N ammonia. The product obtained (1.94 grams) was separated into each of the anomers at the 1-position by chromatography on silica by means of a mixture of chloroform-methanol-ammonia (2:2:0.5). 450 mg of the β-anomer and 930 mg of the α-anomer were obtained.

Anomer α: Rf =0.15 (silica, chloroform-methanol-ammonia 2:2:0.5).

Anomer β: Rf = 0.3 (silica, chloroform-methanol-ammonia 2:2:0.5).

The 1-0-acetyl 2-0-benzyl 3-(N-carbethoxy N-methyl) amino 3,4,6-tridesoxy D-xylohexopyranose used in stage B was prepared according to the following example Stage 1: Ethyl 3-(N-carbethoxy N-methyl) amino 3,4,6-tridesoxy D-xylohexopyranoside Sixty-seven grams of ethyl 3-(N-carbethoxy N-methyl) amino 3,4,6-tridesoxy 2-0-ethoxycarbonyl D-xylohexopyranoside (prepared according to J. Org. Chem., 1965, 30, 1287) are dissolved in 500 ml of ethanol, then 200 ml of 2N soda (sodium hydroxide) added thereto. The mixture is stirred for one hour at room temperature, then diluted with water and extracted with methylene chloride. The organic phase is rinsed with water and evaporated until dry in a vacuum to obtain 57 grams of the expected product in the form of a yellow oil which is used as is in 2.

Stage 2: Ethyl 2-0-benzyl 3-(N-carbethoxy N-methyl) amino 3,4,6-tridesoxy D-xylohexopyranoside.

Twelve grams of sodium hydride, dispersed in mineral oil, are placed in suspension in 300 ml of tetrahydrofuran. The solution of 57 g. of the product obtained in the preceding stage is added, under agitation, to 100 ml of tetrahydrofuran. It is heated to boiling and refluxed for 15 minutes, then cooled to 25°C. 29 ml of benzyl bromide are added and left for 15 hours at room temperature. The mixture is diluted with water and extracted with ethyl acetate. After evaporation of the ethyl acetate, the oil obtained is chromatographed on silica by means of a mixture of benzene-ethyl acetate (8:2). 60 G. of the expected product are obtained in the form of a white crytalized solid, m. pt. 65 °C.

Stage 3: 1-0-acetyl 2-0-benzyl 3-(N-carbethoxy N-methyl) amino 3,4,6-tridesoxy D-xylohexopyranose.

Gaseous hydrochloric acid is bubbled into a mixture of 600 ml of acetic acid and 60 ml of acetic anhydride at 25°C. until saturation is completed. Then 60 g. of the product obtained in the preceding stage are added and left for 16 hours at room temperature while continuing bubbling of the hydrochloric acid into the mixture. The mixture is then evaporated until dry in a vacuum not exceeding 40°C.

The oil obtained is chromatographed on silica by means of a mixture of chloroform acetone (9:1). As a result 60 g. of the expected product are obtained in the form of a white crystallized solid.

The α anomer has been obtained in pure form by recrystallization from isopropyl ether. M,P, 87° C.

Analyses: ($C_{19}H_{27}NO_6$)
Calculated: C%62.45 H%7.45 N%3.83
Found: 62.7 7.7 3.7

EXAMPLE 2

4-0(2',6'-diamino 2',3',4',6'-tetradesoxy α,D-erythrohexopyrannosyl) 6-0-(3''-methylamino 3'',4'λ',6''-tridesoxy α,D-xylohexopyrannosyl) 2-desoxy streptamine sulfate 930 mg of the α-anomer obtained by the preceding example is dissolved in 15 ml of water. The solution is neutralized with normal sulfuric acid and the neutralization followed with a pH meter. About 8.4 ml of acid is used. Activated carbon is added to the solution, the mixture is filtered and the filtrate concentrated under vacuum. Upon addition of methanol, the sulfate is precipitated to obtain 1.24 grams of the titled sulfate in the form of a white solid having the formula $C_{19}H_{39}N_5O_6$, 5/2 $H_2SO_4$. $[\alpha]_D^{20} = =91°$ (c = 0,6% water).

EXAMPLE 3

An injection preparation is prepared as follows:

| | |
|---|---|
| - Final product of Example 1 | 50 mg |
| - Sterile aqueous excipient | 1 ml |

- Pharmacalogical Study - a. In vitro antibacterial activity

The antibacterial activity has been measured in vitro by the dilution method in liquid medium.

A series of tubes is prepared in which is distributed the same quantity of nutritive medium. Increasing quantities of the antibiotic under study are distributed, then each tube is inoculated with a bacterial strain as indicated in the table. After a 24 or 48 hour incubation in a 37° oven, inhibition of the bacterial growth is appraised by transillumination which determines the minimal inhibiting concentration (CMI) of the products expressed as ug/ml in the table. In the following table, the product of example 1 is identified as Product A and the Product of example 2, Product B.

| STRAINS | Product A | |
|---|---|---|
| | 24H | 48H |
| Staphylococcus Oxford U.C. 1061 penicillino-sensible | 0.5 | 0.5 |
| Staphylococcus aureus U.C. 1128 penicillino-resistant | 0.5 | 0.5 |
| Streptococcus hemolyticus 905 | 20 | 40 |
| Streptococcus faecalis 5432 | >100 | — |
| Bacillus subtilis | ≤0.02 | 0.05 |
| Escherichia Coli U.C. 1020 | 2 | 2 |
| Pseudomonas pyocyanea 7403 | 5 | 10 |
| Klebsiella pneumoniae 52145 | 0.2 | 0.2 |
| Proteus mirabilis A 235 | 2 | 2 |

| STRAINS | Product B | |
|---|---|---|
| | 24H | 48H |
| Staphylococcus aureus 4546 | 0.4 | 0.6 |
| Staphylococcus aureus 5159 | 0.6 | 1 |
| Staphylococcus aureus 397 | 0.2 | 0.2 |
| Enterobacter aerogenes 6086 | 1 | 1 |
| Enterobacter cloaca 681 | 0.6 | 0.6 |
| Proteus vulgaris A 232 | 5 | 10 |
| Proteus morganii A 236 | 3 | 5 |
| Pseudomonas pyocyanea 8054 | 15 | 20 |
| Pseudomonas pyocyanea W 13 2393 | 10 | 20 |
| Pseudomonas pyocyanea W 4 8429 | 5 | 10 |
| Pseudomonas pyocyanea 7468 | 3 | 5 |
| Escherichia Coli 8679 | 0.6 | 1 |
| Escherichia Coli 7693 | 1 | 1 | b. In vivo antibacterial activity:

The antibacterial activity has been measured in vivo on an experimental Staphylococcus Aureus 54146 infection.

90 mice with a medium weight of 22 grams were divided in 9 series of 10 mice. An intraperitoneal infection with 0.5 ml of a Staphylococcus Aureus 54146 culture in Pasteur nutritive bouillon diluted to one quarter with sterile water is conducted. Treatment is performed by subcutaneous adminstration of Product B three times, (1 hour, 5 hours and 23 hours) after infection. The mortality rate at different times as indicated in the table was measured as well as the number of mice surviving after 8 days.

The results are summarized in the following table.

| DOSAGE | Mortality at | | | | | | | Survived to the eighth day |
|---|---|---|---|---|---|---|---|---|
| | 5 H | 7 H | 22 H | 48 H | 56 H | 72 H | 94 H | 168 H | |
| Distilled water | 1 | 7 | 2 | — | — | — | — | — | 0 |
| Product B (0.1 mg) | | 1 | 6 | 1 | 1 | 1 | — | | 0 |
| Product B (0.2 mg) | | | 1 | | | 2 | 1 | | 6 |
| Product B (0.3 mg) | | | | | | | | | 10 |
| Product B (0.4 mg) | | | | | | | | | 10 |

The foregoing results clearly demonstrate the good activity of Products A and B of the invention.

What is claimed is:

1. The 4-0-(2',6'-diamino 2',3',4',6'-tetradesoxy α,D-erythrohexopyrannosyl) 6-0-(3''-methylamino 3'',4'',6''-tridesoxy α,D-xylohexopyrannosyl) 2-desoxystreptamine of the formula:

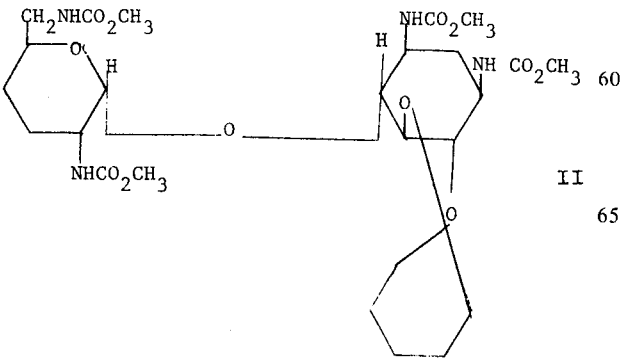

and its pharmaceutically acceptable salts.

2. A product according to claim 1 wherein the pharmaceutically acceptable salts are formed from sulfuric acid, hydrochloric acid, phosphoric acid, hydrobromic acid, nitric acid, succinic acid, tartaric acid, formic acid, acetic acid, citric acid, oxalic acid, benzylic acid, glyoxylic acid, aspartic acid, benzoic acid, para-toluenesulfonic acid, fumaric acid, maleic acid, or methanesulfonic acid.

3. A product according to claim 1 which is the sulfate of 4-0-(2',6'-diamino 2',3',4',6'-tetradesoxy α D-erythrohexopyrannosyl) 6-0-(3''-methylamino 3'',4'', 6''-tridesoxy α,D-xylohexopyrannosyl) 2-desoxystreptamine.

4. A process for the preparation of the product of claim 1 which comprises reacting a compound of the formula:

with an acidic agent selected from the group consisting of acidic ion exchange resin, and an aqueous solution of a mineral or organic acid to obtain the product of the formula:

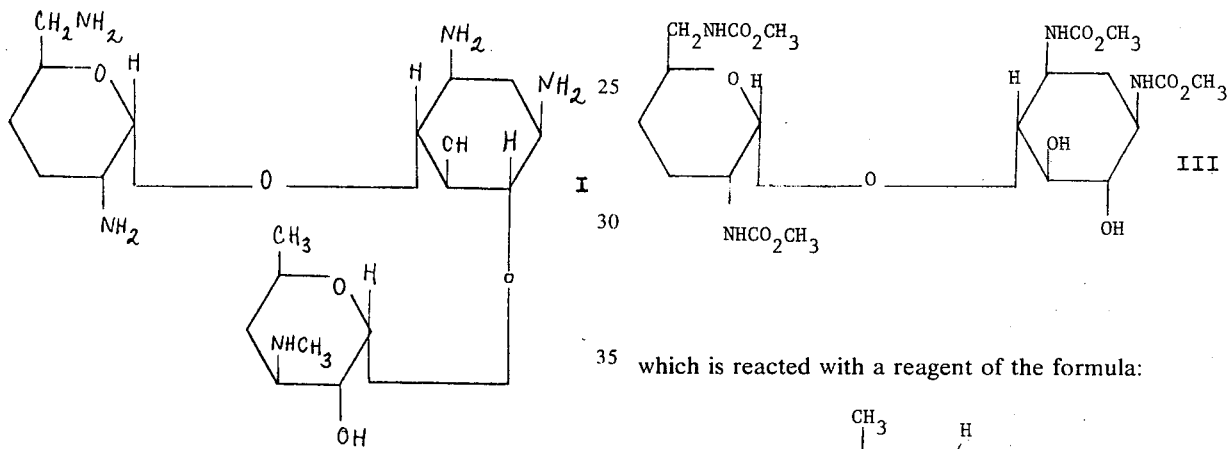

which is reacted with a reagent of the formula:

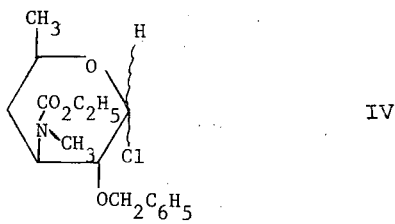

in the presence of a catalyst to obtain the corresponding product in the form of a mixture of α anomer of the formula:

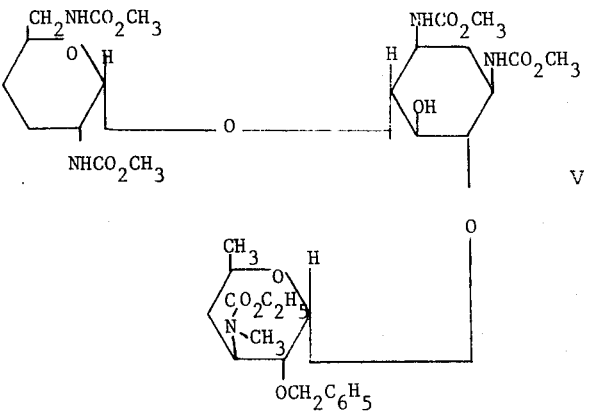

and the β anomer of the formula:

[Structure VI]

reducing this mixture with hydrogen in the presence of a catalyst to obtain a mixture of products having the formula:

[Structure VII]

and

[Structure VIII]

which mixture is treated with an alkaline agent selected from the group consisting of an aqueous solution of baryta, sodium hydroxide and potassium hydroxide to obtain a mixture of products having the formula:

[Structure I]

and

[Structure IX]

and separating the product of claim 1 from the mixture, which can then be converted to a pharmaceutically acceptable salt.

5. A process for the preparation of the product of claim 1 which comprises reacting a compound of the formula:

[Structure II]

with an acidic agent selected from the group consisting of acidic ion exchange resin, and an aqueous solution of a mineral or organic acid to obtain the product of the formula:

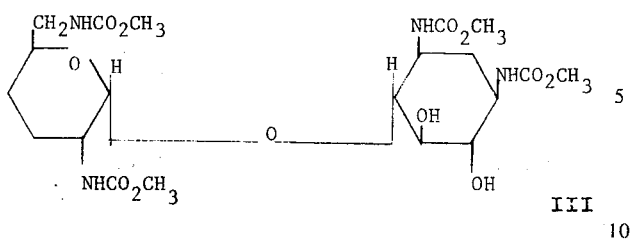

III which is reacted with a reagent of the formula:

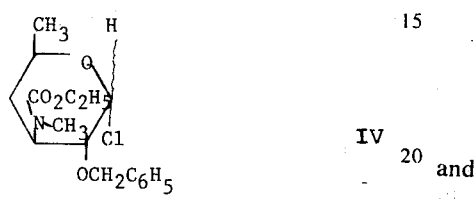

IV in the presence of a catalyst to obtain the corresponding product in the form of a mixture of α anomer of the formula:

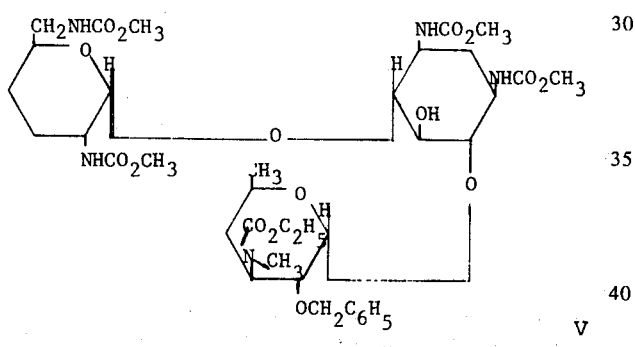

V and the β anomer of the formula:

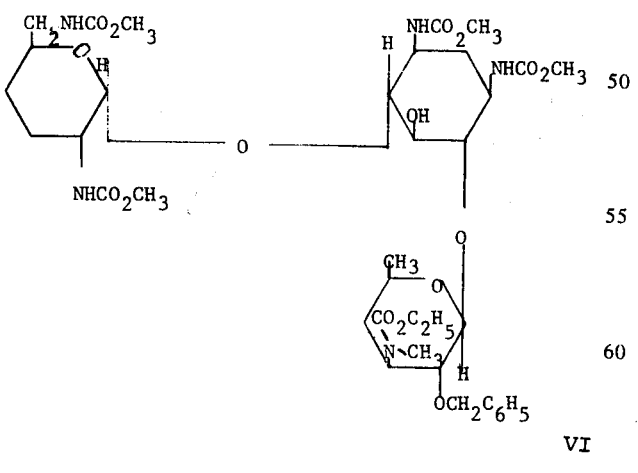

VI reducing this mixture with hydrogen in the presence of a catalyst to obtain a mixture of products having the formula:

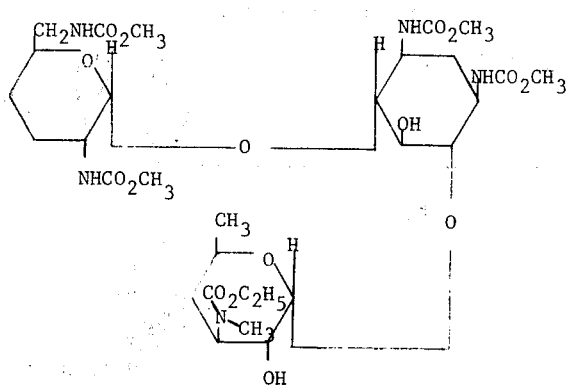

VII and

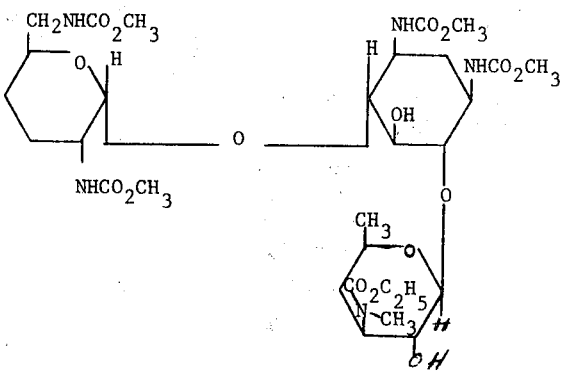

VIII the product of formula VII is then isolated and treated with an alkaline agent selected from the group consisting of an aqueous solution of baryta, sodium hydroxide and potassium hydroxide to obtain a product having the formula:

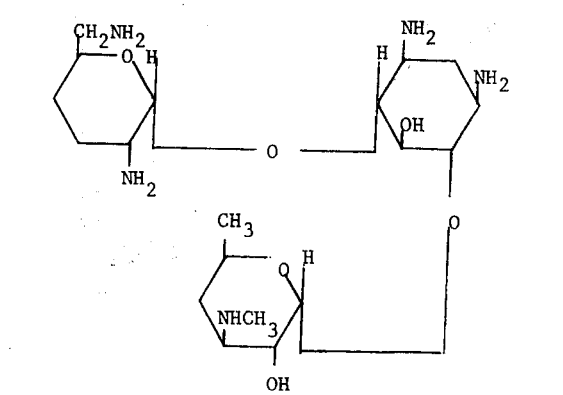

I which can be converted to a pharmaceutically acceptable salt.

* * * * *